United States Patent [19]

von Blücher et al.

[11] Patent Number: 4,610,905

[45] Date of Patent: Sep. 9, 1986

[54] YARN HAVING SPECIFIC PROPERTIES

[76] Inventors: Hubert von Blücher, Freytagstrasse 45; Hasso von Blücher, Sohnstrasse 58, both of D-4000 Düsseldorf; Ernest de Ruiter, Höhenstrasse 57a, D-5090 Leverkusen 3, all of Fed. Rep. of Germany

[21] Appl. No.: 553,215

[22] Filed: Nov. 18, 1983

[30] Foreign Application Priority Data

Nov. 24, 1982 [DE] Fed. Rep. of Germany ....... 3243484

[51] Int. Cl.$^4$ .................... B32B 5/02; B32B 27/02
[52] U.S. Cl. ........................................ 428/90; 57/244; 57/251; 428/224; 428/368; 428/372; 428/373; 428/400; 428/902; 428/921; 87/8
[58] Field of Search ............. 428/375, 921, 372, 373, 428/374, 368, 400, 902, 90; 87/8; 57/901, 242, 243, 244, 251

[56] References Cited

U.S. PATENT DOCUMENTS

| | | | |
|---|---|---|---|
| 3,968,283 | 7/1976 | Schutte | 428/373 |
| 4,154,881 | 5/1979 | Hirakawa et al. | 428/373 |
| 4,351,878 | 9/1982 | Harper-Ternet et al. | 428/375 |
| 4,388,370 | 6/1983 | Ellis et al. | 428/373 |
| 4,397,907 | 8/1983 | Rosser et al. | 428/244 |
| 4,438,178 | 3/1984 | Powers | 428/375 |
| 4,500,593 | 2/1985 | Weber | 428/373 |

*Primary Examiner*—Paul J. Thibodeau
*Attorney, Agent, or Firm*—Sprung Horn Kramer & Woods

[57] ABSTRACT

Textile flat-shaped structures exhibiting specific properties, such as flame-resistance or adsorbing capacity, are required for technical purposes, said structures being at the same time characterized by a high flexibility and tensile strength, as well as good wearing characteristics when used for protective suits. This is achieved by the invention by yarns that are sheathed with active ingredients, such as adsorbents, fire-proofing agents, ion-exchangers, decontaminating agents for chemical combat agents, catalysts or fixed enzymes. The active ingredients are adhered to the surface of the yarn or embedded in a binding agent. The sheathing may be additionally braided or flocked.

20 Claims, No Drawings

YARN HAVING SPECIFIC PROPERTIES

The invention relates to yarns containing active ingredients having specific properties present in a layer sheathing the yarn. The invention relates further to the use of said yarns for the manufacture of flat-shaped textile structures, flexible flat-shaped filters or protective suits and articles manufactured by using said yarns.

Flat-shaped textile filters exhibiting adsorbing properties are employed in the most different technical fields. They are used, for example, in hoods for kitchens, in air-conditioning installations for buildings or vehicles, in masks or protective suits against toxic agents.

There are basically two different types of flat-shaped filters. A conventional type consists of a tissue or non-woven fabric, for example, of cellulose or PAC fibers, the tissue or the non-woven fabric being first carbonized and thereafter activated. A flat-shaped filter of the kind exhibits a high activity, but the tensile strength is often not sufficient, thus, restricting its application in many fields. For this reason, one started to provide this type of flat-shaped filter in a so-called sandwich configuration, embedded between two non-woven fabrics, however, the use of this flat-shaped filter was still substantially confined to stationary plants.

For instance, flat-shaped filters of adequate flexibility and at the same time high tensile strength are required for the manufacture of protective suits. Prior art flat-shaped filters employed to this end consist of a flexible carrier material loaded with adsorbers, e.g. a textile tissue, a fleece or a foam material. In order to "load" the carrier materials with substances exhibiting protective and/or adsorbing properties, it is necessary to provide binders to make these substances stick to the carrier material. The binder, however, simultaneously fills up a considerable part of the pore volume of the carrier material whereby the activity of the flat-shaped filters is reduced and becomes often insufficient.

Flame-resistant flat-shaped textile structures play an important part as preventive protection in the equipping of hotel rooms, theaters and congress halls, as well as in busses and aircrafts. Apart from flame-resistant materials which respond only to one fiber, e.g. cellulose fibers or wool, all other fire-proofing agents adversly change the character of textile materials. The feel becomes hard and the capacity to allow air and water vapor to pass therethrough, or even to only transport moisture, is strongly impaired. As a result thereof the wearability suffers considerably. The reason for this behavior is attributed in particular to the binder that fixes the pigment-type flame-proofing agent, but also causes the tissue to become tacky.

The object of the invention is to provide flat-shaped textile structures having specific properties, such as flame-resistance or adsorbing capacity which combine a good flexibility and tensile strength with a high activity for the desired active ingredients, thus making them suitable for use in a wide range of applications, e.g. as flat-shaped filter, or for improving the wearability of protective suits.

This is achieved according to the invention by providing a yarn in which the active ingredients responsible for the specific characteristics are present in a layer surrounding said yarn. Subject matter of the invention are also flat-shaped textile structures prepared by means of said yarn, in particular flexible flat-shaped filters or protective suits.

The active ingredients responsible for the specific properties which are present in the layer surrounding the yarn may be adsorbents, in particular activated carbon, fire-proofing agents, in particular radical scavengers or insulating layer-forming agents, decontaminating agents for chemical combat agents, ion-exchangers, graphite-or metall powder, katalysts or fixed enzymes.

The active ingredients may be fixed on the carrier yarn by means of a binder or an adhesive, or may be embedded in the binder.

The sheathed yarn is preferably additionally braided or flocked.

The carrier yarn is not subject to any restrictions, neither in respect of its structure, nor its chemical nature. It must only exhibit sufficient tensile strength and a certain "roughness" and structure or texture to ensure a good adhesion of the sheathing thereto. The carrier yarn may be both a monofilament or a multifilament yarn comprising mineral, synthetic or natural fibers. The use of flame-resistant yarns exhibiting a high tensile strength consisting of aramides (KEVLAR and NOMEX) or polyimides may be useful for certain purposes. Also metal fibers or metallized yarns may serve as carrier yarns.

The binders or adhesives for fixing the active ingredients on the yarn are in particular polymer binders, such as polyurethane or polyacrylate latices, the latex of, if desired, halogenated elastomers, such as natural, synthetic or silicon rubber, chloroprene or fluoroprene. In order to remove the volatile latex components, these coatings must be dried in a subsequent process step. When this takes place, depends on the function that the binder or adhesive has still to fulfill. If the active ingredients are intended to adhere only exteriorily to the adhesive, the drying will, depending on the type of adhesive, be conducted before or after applying the active ingredients. If, however, the active ingredients are applied in mixture with the binder, i.e. are embedded in the binder, and the latter is additionally intended to serve for anchoring the flocks of fibers, the drying is conducted preferably with the sheathed and exteriorily flocked yarn.

Depending on the chemical nature of the binder and the further processing, also a heat treatment for cross-linking or vulkanizing the polymer binder may be conducted in addition to the drying. Fusion adhesives consisting mainly of polyamides, polyesters or ethylene-vinyl acetate copolymers (EVA) are paticularly suitable to this end. For the purposes of the invention, these substances are applied predominantly as dispersion. The amount of binder may be in the range of from 5 to 200, in particular from 10 to 100 percent by weight, based on the active ingredient.

Depending on the kind of use, the yarn may first be sheathed by an adhesive and thereafter supplied with the active ingredients; alternatively, the yarn may be directly sheathed with a paste comprising the binder and the active ingredients. Particularly useful apparatuses for applying the adhesive or the paste are of the kind employed for applying the flock adhesive or flock binder in the yarn flocking step. They usually consist of a through wherein the yarn is wetted, a pair of rolls exhibiting grooves that strip off surplus adhesive and a drying installation. In the event that the powdery active ingredients are intended to adhere exteriorily to the adhesive, on the fiber, the drying will, of course, be conducted after applying the active ingredient.

The yarn which has been sheathed in one way or the other by the active ingredients is subsequently braided or flocked to ensure better processing and to increase the abrasive resistance. The braiding of the sheathed yarn with a continuous yarn of a fine denier is conducted in a conventional manner, such as used for the braiding of elastomer threads of corsetry. The appearance of the yarn is basically determined by the braiding. The further processing to flat-shaped textile structures will also be much easier if the yarn is braided, in particular when the sheathing is relatively rough.

Instead of braiding, the yarn sheathed with the active ingredients may be alternatively flocked for the same reason as the braiding, namely coloration, protection of the sheathing and improvement of processability. The flocking may be carried out in one with the applying of the active ingredients to the flock binder or directly after applying the paste which consists of active ingredient and binder, i.e. prior to drying the sheathing. In the latter case a high content of the active ingredients in the sheathing may require an additional layer of adhesive. The flocking takes place in a conventional manner using short-stalked monofilament textile fibers having a length down to fractions of millimeters, and mostly electrostatically. Basically all natural and synthetic fibers may used as flocking material. The fiber dust substantially consists of cotton, wool, silk, viscose, rayon or polyamide fibers.

In a preferred embodiment of the invention, the active ingredient is an adsorbent, in particular activated carbon. Conventional adsorbing materials, such as silica xerogels, metal oxides and hydroxides, in particular aluminium oxide and hydroxide, molecular sieves, ion-exchangers and activated carbons of different origins, may also be employed. The activated carbon may be prepared from suitable organic materials in a manner known per se. For example, a particularly suitable activated carbon can be obtained by carbonizing ion-exchangers consisting mainly of polystyrol and subsequently activating the same with water vapor. The inner and outer surfaces of the adsorbents may be loaded with additives, such as heavy-metal catalysts or flame-resistant anti-bacterial or fungicide substances.

It might be useful for processing and practice to surround the adsorbent particles, in particular activated carbon particles, with a thin layer of polymers exhibiting a selective permeability for the substances being adsorbed. Thus, it is possible to surround, for example, activated carbon particles, with a thin film of macromolecules by pretreatment with acrylate dispersions, e.g. Acronal 50D and 27D of BASF, said film being pervious to combat agents, but not to numerous substances which have a blocking effect on the activated carbon, such as sweat. Another possibility of encapsulating the adsorbent particles is to subject the same to a turbulence in a two-component blower with a polyamide powder, if possible of the same particle size, approximately at a quantitative ratio of 1:1 and to catapult the same through a tubular gas-fired furnace, against a cooled mirror chrome-plated sheet-steel. The polyamide softened in the tubular gas-fired furnace encloses in the hot air stream the adsorbent particles and solidifies as it issues out of the furnace in the cooled air current.

A sticking of the polyamide-sheathed adsorbent particles to each other is prevented by the impingement upon the mirror chrome-plated sheet-steel which is cooled down to about $-15°$ C. Other conventional methods for micro-encapsulating the adsorbent particles with various inorganic or organic sheathing materials may equally be applied. By virtue of the encapsulation, it is achieved that the binding agent does not have a blocking effect on the activated carbon in case a paste consisting of powdered activated carbon and a binder is used for the sheathing. In order to ensure a high activity, the pulverulent adsorbent is in this case very finely ground and has a particle size of only from 0.01 to 50 $\mu$m, preferably from 1 to 10 $\mu$m. With the help of a jet mill, it is possible to grind, for instance the activated carbon, to particle sizes of 95% below 3 $\mu$m. Activated carbons of the kind may have predetermined pore sizes and at the same time a very large activated surface of up to 1,400 m$^2$/g. If the adhesive is first applied on the yarn and the activated carbon thereafter fixed therein, particles of from 10 to 100 $\mu$m are preferred, depending on the thickness of the yarn. Fine powder ought to be avoided because it may cover the adhesive layer.

If according to another embodiment of the invention, catalysts, in particular metal oxides, ion-exchangers, molecular sieves or pigment-type fire-proofing agents are used as the acitive ingredient for the sheathing, the method of application and particle size mentioned in connection with the adsorbents, in particular the activated carbon, will equally apply.

As to the fire-proofing agent which can be employed as active ingredient, the invention is subject to practically no restrictions. Carbonization promoting and fire-extinguishing, as well as barrier layer-forming, fire-proofing agents, or radical scavengers may equally be used. Preferred agents are the so-called insulating layer-forming agents which contain substances that swell like a foam upon heating, are carbonized up to from 200° to 300° C. and thereby solidify to form a fine-pored padding with good insulating characteristics. Useful are also the fire-proofing agents familiar in connection with plastic materials, the flame-resistant effect of which being enhanced by so-called synergetic agents or specific plasticizers and binders which are necessary in particular in the case of pigment-type fire-proofing agents. Also self-extinguishing plastic materials, in particular those exhibiting a high halogen content, may be employed alone or in combination with other prior art fire-proofing agents. Summarizing, all fire-proofing agents may be used within the scope of the invention which are compatible with the textile structure serving as carrier and with each other and, for example, are described in Römpps "Chemie-Lexikon", 8th edition, (1981) under the keyword "Flammschutzmittel" and in the references cited herein. The insulating layer-forming agents that swell foam-like under the influence of heat form a non-inflammable insulating foam which, in case of emergency, gushes forth, also under the braiding or flocking, and seals the tissue made of said yarn against hot gases.

Analogous to adsorbents or flame-proofing agents, also chemicals may be embedded in the sheathing as active ingredient, said chemicals being able to destroy chemical combat agents so that one can manufacture therefrom a self-decontaminating protective suit. The skilled artisan will select binding agents and yarns that are compatible with the chemicals employed. Yarns sheathed with ion-exchangers lend themselves to the manufacture of flat-shaped structures and flat-shaped filters exhibing exchanging properties. In a similar manner, flat-shaped stuctures possessing catalytic properties may be manufactured which are suitable for catalytic processes that do not require elevated temperatures.

Enzymes which are often called organic catalysts but are more specific and efficient than conventional catalysts deserve special attention. Enzymes need, however, water to display their activity. One possibility to overcome this difficulty is to encapsulate the gel droplet containing the enzyme and to use this microcapsules in the sheathing. The encapsulation is designed to preserve the gel, but should not be allowed to inhibit the reaction with the enzyme. There are enzymes which specifically attack chemical combat agents belonging to the group of paralysants; in this case, an encapsulation with hydrophobic or oleophilic properties is preferably selected to allow the combat agent to penetrate. Flat-shaped filters loaded with enzymes lend themselves to protective suits (C-protection, paralysants) industrial filters, air-conditioning installations etc. Another variant of an enzyme-containing sheathing is obtained by first surrounding the yarn with a spongy layer—a layer of the kind was obtained, for example, by a coagulated urethane—in which the enzyme-containing gel is embedded. It is recommended to employ a hydrophobic cover layer to protect the gel, the mode of operation of which being already described in connection with the encapsulation. Finally, it was found that the gel may be stabilized vis a vis moisture by adding non-volatile hygroscopic substances of the most different kinds which, however, should not impair the pH-value or the reaction mechanism so that, depending on the field of application, the gel-protecting layer may be dispensed with.

Finally, also activated carbon may be employed as carrier for enzymes or for enzymes embedded in a resin matrix. It is familiar to those skilled in the art that enzymes must be protected against microorganisms.

The thickness of the sheathing substantially depends on the thickness of the carrier yarn and is approximately of the same magnitude. Preferred yarns are those having a thickness of from 5 to 100 denier, depending on the purpose for which they are used, the smaller yarn diameter being selected for clothing and the greater yarn diameter e.g. for industrial filters. The thickness of the sheathing amounts in particular to from 25 to 300% of the yarn diameter.

The sheathed, in particular additionally braided or flocked yarn is then processed to form a flat-shaped textile structure. The preferred kind is a tissue in which the adsorbing threads constitute the chain. All chain threads may be sheathed threads according to the invention or other kinds of chain threads may be used therewith. The color of the tissue is determined by the weft and the material employed for braiding or flocking. The so-obtained tissues result in, e.g. flat-shaped filters exhibiting up to 100g activated carbon per square meter. The textile and physiological properties allow to manufacture therefrom excellent protective suits against chemical combat agents.

We claim:

1. An adsorptive yarn comprising
(a) a yarn constituting a core,
(b) a sheath surrounding the core yarn (a) and comprising a binder having embedded therein activated carbon particles, the sheath thickness ranging from 25 to 300% of the core diameter, the binder being present in from 5 to 200 percent by weight of the carbon particles, and
(c) a fiber flock held to the sheath (b) by its binder and imparting to the overall yarn textile-yarn feel, appearance and performance.

2. A yarn according to claim 1, wherein the core comprises an aramide fiber.

3. A textile formed from a yarn according to claim 1.

4. A protective article of clothing made from a textile fabric according to claim 1.

5. A yarn according to claim 1 further containing a fixed enzyme carried by the activated carbon particles.

6. A reactive yarn comprising
(a) a yarn constituting a core,
(b) a sheath surrounding the core yarn (a) and comprising a binder having embedded therein particles of a flame-retardant, the sheath thickness ranging from 25 to 300% of the core diameter, the binder being present in from 5 to 200 percent by weight of the flame-retardant particles, and
(c) a fiber flock held to the sheath (b) by its binder and imparting to the overall yarn textile-yarn feel, appearance and performance.

7. A yarn according to claim 6, wherein the core comprises an aramide fiber.

8. A textile formed from a yarn according to claim 6.

9. A protective article of clothing made from a textile fabric according to claim 6.

10. A yarn according to claim 6 wherein the flame retardant comprises a radical scavenger or an insulating layer-forming agent.

11. An adsorptive yarn comprising
(a) a yarn constituting a core,
(b) a sheath surrounding the core yarn (a) and comprising a binder having embedded therein activated carbon particles, the sheath thickness ranging from 25 to 300% of the core diameter, the binder being present in from 5 to 200 percent by weight of the carbon particles, and
(c) a textile yarn held to the sheath by core-yarn spinning and imparting to the overall yarn textile-yarn feel, appearance and performance.

12. A yarn according to claim 11, wherein the core comprises an aramide fiber.

13. A textile formed from a yarn according to claim 11.

14. A protective article of clothing made from a textile fabric according to claim 11.

15. A yarn according to claim 11 further containing a fixed enzyme carried by the activated carbon particles.

16. A reactive yarn comprising
(a) a yarn constituting a core,
(b) a sheath surrounding the core yarn (a) and comprising a binder having embedded therein particles of a flame-retardant, the sheath thickness ranging from 25 to 300% of the core diameter, the binder being present in from 5 to 200 percent by weight of the flame-retardant particles, and
(c) a textile yarn held to the sheath by core-yarn spinning and imparting to the overall yarn textile-yarn feel, appearance and performance.

17. A yarn according to claim 16, wherein the core comprises an aramide fiber.

18. A textile formed from a yarn according to claim 16.

19. A protective article of clothing made from a textile fabric according to claim 16.

20. A yarn according to claim 16 wherein the flame retardant comprises a radical scavenger or an insulating layer-forming agent.

* * * * *